United States Patent
Evers et al.

(10) Patent No.: US 10,393,735 B2
(45) Date of Patent: Aug. 27, 2019

(54) PROCESSING OF FLUIDS CONTAINING INTERFERING PARTICLES

(71) Applicant: KONINKLIJKE PHILIPS N.V., Eindhoven (NL)

(72) Inventors: Toon Hendrik Evers, Eindhoven (NL); Ron Martinus Laurentius Van Lieshout, Geldrop (NL); Joannes Baptist Adrianus Dionisius Van Zon, Waalre (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 981 days.

(21) Appl. No.: 14/410,275

(22) PCT Filed: Jun. 20, 2013

(86) PCT No.: PCT/IB2013/055079
§ 371 (c)(1),
(2) Date: Dec. 22, 2014

(87) PCT Pub. No.: WO2014/001985
PCT Pub. Date: Jan. 3, 2014

(65) Prior Publication Data
US 2015/0323523 A1    Nov. 12, 2015

Related U.S. Application Data

(60) Provisional application No. 61/665,925, filed on Jun. 29, 2012.

(51) Int. Cl.
*G01N 31/00* (2006.01)
*G01N 33/53* (2006.01)
*G01N 33/543* (2006.01)

(52) U.S. Cl.
CPC . *G01N 33/54333* (2013.01); *G01N 33/54326* (2013.01)

(58) Field of Classification Search
None
See application file for complete search history.

(56) References Cited

U.S. PATENT DOCUMENTS

| 9,387,484 B2 * | 7/2016 | Wimberger-Friedl .... B03C 1/01 |
| 2002/0155511 A1 | 10/2002 | Horrocks et al. |
| 2007/0224700 A1 | 9/2007 | Masters |
| 2011/0098623 A1 | 4/2011 | Zhang et al. |
| 2011/0223583 A1 | 9/2011 | Gordon |
| 2011/0244443 A1 | 10/2011 | Van Rijn et al. |
| 2011/0262919 A1 | 10/2011 | Tajima |

FOREIGN PATENT DOCUMENTS

| JP | 9218201 A | 8/1997 | |
| WO | 200212896 A1 | 2/2002 | |
| WO | 2005010542 A2 | 2/2005 | |
| WO | 2005010543 A1 | 2/2005 | |
| WO | 2008044214 A1 | 4/2008 | |
| WO | 2008072156 A2 | 6/2008 | |
| WO | 2008115723 A1 | 9/2008 | |
| WO | 2008155716 A1 | 12/2008 | |
| WO | 2009016533 A2 | 2/2009 | |
| WO | 2010057318 A1 | 5/2010 | |
| WO | WO 2010/057318 A1 * | 5/2010 | ............... G01N 1/40 |
| WO | 2011159707 A1 | 12/2011 | |
| WO | WO 2011/159707 A1 * | 12/2011 | ............ G01N 33/543 |

OTHER PUBLICATIONS

Hou et al. (Micromachines, 2011, vol. 2, pp. 319-343).*
Davis et al. (PNAS, Oct. 3, 2006, vol. 103., No. 40., pp. 14779-14784).*
Issadore et al. (Lab on a Chip, Jan. 2011, vol. 11, No. 1, pp. 147-151).*
Yung et al. (Lab on a Chip, vol. 9, No. 9., May 7, 2009, pp. 1171-1177).*
Shim etal. (Biomed Microdevices, 2010, vol. 12., pp. 949-957).*
S. Roath, "Biological and biomedical aspects of magnetic fluid technology", Journal of Magnetism and Magnetic Materials 122 (1993), pp. 329-334.
Mehmet Toner et al, "Blood-On-A-Chip", Annu. Rev. Biomed. Eng. 2005, 7:77-103, doi: 10.1146/annurev.bioeng.7.011205.135108.
Charles S. Owen, "High Gradient Magnetic Separation of Erythrocytes", Biophysical Journal, vol. 22, 1978, pp. 171-178.
Gubin, S.P. et al "Magnetic nanoparticles: preparation, structure and properties", Russian Chemical Reviews, vol. 74, No. 6, 2005, pp. 489-520.

* cited by examiner

*Primary Examiner* — Lisa V Cook

(57) ABSTRACT

The invention relates to a method and a processing device for the processing of a fluid containing interfering particles (C). Magnetic particles (MP) are added to the fluid in a processing chamber and distributed, in part, using a magnetic field to provide a blocking zone (BZ) within the processing chamber to impede or prevent such migration of the interfering particles (C) through the processing chamber. The blocking zone (BZ) hence acts as a filter element by which interfering particles (C) can for example be kept away from a detection region at the surface of the processing chamber.

9 Claims, 5 Drawing Sheets

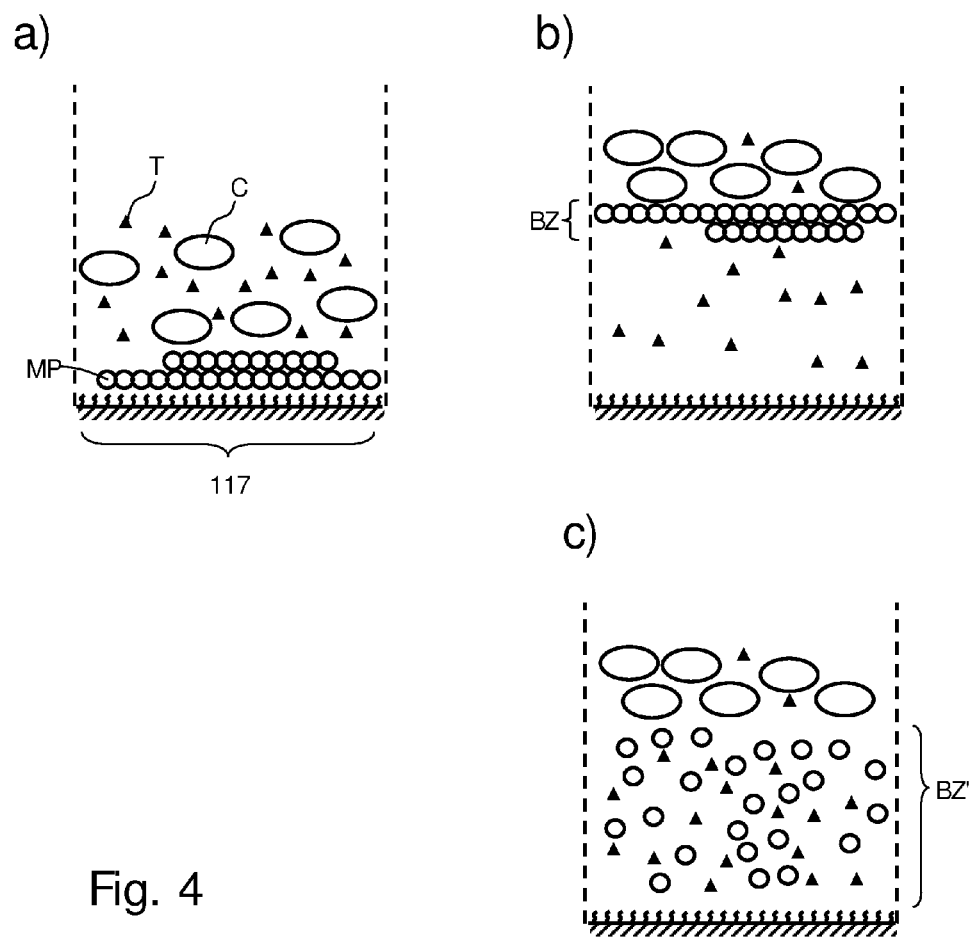
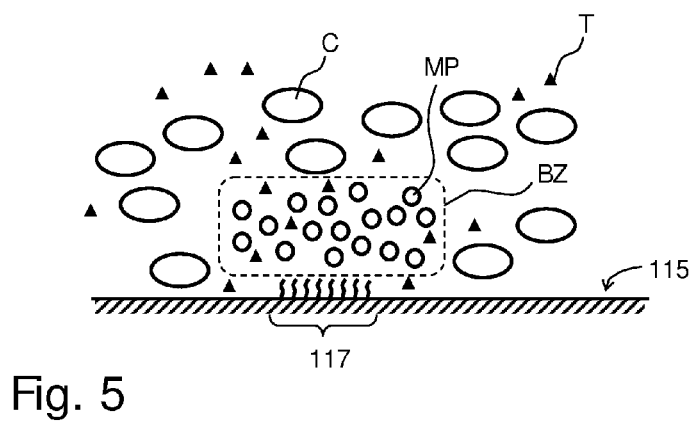
Fig. 4
Fig. 5

PROCESSING OF FLUIDS CONTAINING INTERFERING PARTICLES

CROSS-REFERENCE TO PRIOR APPLICATIONS

This application is the U.S. National Phase application under 35 U.S.C. § 371 of International Application No. PCT/IB2013/055079, filed on Jun. 20, 2013, which claims the benefit of U.S. Provisional Patent Application No. 61/665,925, filed on Jun. 29, 2012. These applications are hereby incorporated by reference herein.

FIELD OF THE INVENTION

The invention relates to a method and a processing device for the processing of a fluid containing particles that interfere with the processing.

BACKGROUND OF THE INVENTION

The WO 2008/044214 A1 discloses a biosensor for the detection of target components in a sample fluid. Magnetic particles are provided as dry reagents in a layer on top of a surface with capture antibodies. When the sample fluid is added, the magnetic particles are rapidly solved and distributed within the whole fluid such that binding sites on the magnetic particles can bind to target components of the sample. The magnetic particles are then attracted by magnetic forces to the capture antibodies, where further binding takes place. Target components bound to the surface are then detected for instance by frustrated total internal reflection (FTIR).

When a sample fluid like whole blood is processed, the target components are often substances of blood plasma while the blood cells are particles which disturb the detection process. Accordingly, samples like blood usually have to be filtered before detection in order to remove disturbing particles.

SUMMARY OF THE INVENTION

It is an object of the present invention to provide means that allow for a simple and highly efficient processing of fluids containing particles which can affect the intended processing.

This object is achieved by a method for processing a fluid containing interfering particles, a processing device having a processing chamber and a magnetic field generator, and a use of the processing device for molecular diagnostics, biological sample analysis, chemical sample analysis, food analysis and/or forensic analysis.

According to a first aspect, the invention relates to a method for the processing of a fluid containing particles. Because said particles are assumed to interfere in some way with the intended processing of the fluid, they will in the following be called "interfering particles" for purposes of reference. While said interference will typically be negative (impeding the processing), the present invention shall also comprise a positive interference in which the interfering particles may support the intended processing or may even be the subject of said processing. The interfering particles may in general comprise single atoms or molecules. Typically, they will however be larger aggregates of atoms having diameters from about a few nanometers up to a millimeter (or more). The interfering particles may have a chemically homogeneous composition or they may be complex aggregates like biological cells. A typical example of a fluid is whole blood, wherein the processing comprises the detection of target components in blood plasma while cells (e.g. red and white blood cells) constitute "interfering particles" which disturb the detection process.

The method of the present invention shall comprise the following steps:

a) Providing the fluid to be processed in a processing chamber. The processing chamber is typically an empty cavity or a cavity filled with some substance like a gel that may absorb a substance; it may be an open cavity, a closed cavity, or a cavity connected to other cavities by fluid connection channels.

b) Providing magnetic particles in the aforementioned processing chamber.

The term "magnetic particles" shall comprise both permanently magnetic particles as well as magnetizable particles, for example superparamagnetic beads. The size of the magnetic particles typically ranges between 3 nm and 50 µm.

c) Distributing the aforementioned magnetic particles in a (two- or three-dimensional) zone—called "blocking zone" in the following—within the processing chamber such that migration of the interfering particles through the blocking zone is impeded, preferably prevented.

It should be noted that the aforementioned steps of the method can be executed in the listed or any other appropriate order. In particular, it is possible to provide the magnetic particles prior to the fluid, or to provide both components simultaneously. The magnetic particles may be provided as dry reagents or as wet reagents (i.e. solved in some carrier fluid). When the magnetic particles are distributed in a blocking zone, they are typically solved in the fluid to be processed.

The "distribution of the magnetic particles in the blocking zone" shall refer to
  the generation of the arrangement of distributed magnetic particles (starting from some other arrangement, e.g. in an aggregated state in a storage region)
  and/or to the maintenance of such an arrangement over an extended (possibly infinite) period of time, particularly during the intended processing step(s).

The described method has the advantage that the distribution of interfering particles within the processing chamber can be controlled via the blocking zone, which affects the migration and hence the spatial distribution of the interfering particles. If the interfering particles negatively affect the intended processing of the fluid, they can thus for example be kept away from the region of processing. If the interfering particles positively affect the processing or are even required for the processing, their concentration may on the contrary be increased in the region of processing. Thus a kind of filtering of the fluid with respect to interfering particles can be achieved by the blocking zone without a need for expensive and space consuming conventional filters.

The distribution of magnetic particles in a blocking zone may for example be driven by diffusion and/or gravity. This is particularly possible if the concentration and amount of magnetic particles is high enough (and the magnetic particles are not too small such that they rapidly diffuse). The magnetic particles will then spread into a cloud that is dense enough to impede the migration of interfering particles and that exists long enough for the intended processing. If gravity directs the magnetic particles towards one surface of the processing chamber, this will stabilize a blocking zone in front of this surface.

According to a preferred embodiment of the invention, a magnetic field is generated that generates and/or maintains the distribution of the magnetic particles in the blocking zone. The magnetic field allows for a direct and easy control of the magnetic particles and their distribution in the blocking zone. Moreover, this way of particle distribution is independent of diffusion and gravity. A blocking zone in front of some surface of the processing chamber may then for example be maintained even if gravity directs the magnetic particles (and interfering particles) away from said surface.

According to a second aspect, the invention relates to a processing device for the processing of a fluid containing interfering particles, said processing device comprising the following components:

A processing chamber in which the fluid and magnetic particles can be provided.

A magnetic field generator for generating a magnetic field in the processing chamber that distributes the magnetic particles in a blocking zone within the processing chamber such that migration of the interfering particles through the blocking zone is impeded. The magnetic field generator may for example comprise a permanent magnet or an electromagnet.

The method and the processing device are different realizations of the same inventive concept, i.e. the control of the migration of interfering particles by a blocking zone of magnetic particles. Explanations and definitions provided for one of these realizations are therefore valid for the other realization, too.

In the following, various preferred embodiments of the invention will be described that relate both to the method and the processing device defined above.

The blocking zone shall impede the migration of the interfering particles in comparison to their migration (i.e. diffusion or gravity) within the remainder of the fluid in the processing chamber. In quantitative terms, this means that the transition rate (particles per s) of interfering particles across some given area outside the blocking zone (but within the processing chamber) shall be larger than the transition rate of interfering particles across an area of same size and shape inside the blocking zone. The transition rate inside the blocking zone may for example be less than about 90%, preferably less than about 50% of the "free" transition rate within the fluid. Most preferably, the impedance is maximal or close to maximal in the sense that the interfering particles cannot migrate through the blocking zone at all (while other components of the fluid can), corresponding to a transition rate of zero.

In general, the migration of interfering particles can be impeded in the blocking zone by any physical and/or chemical effect. In a preferred embodiment, the magnetic particles act just like a conventional filter with pores through which interfering particles can pass or not depending on their size. As the blocking zone will typically have no permanent, static arrangement of the magnetic particles, the pore size of a conventional filter corresponds to the mean distance between neighboring magnetic particles and/or clusters (chains) of magnetic particles in the blocking zone. Preferably, the mean distance "$\Delta$" between neighboring magnetic particles and/or clusters of magnetic particles in the blocking zone should be smaller than five times the mean diameter "d" of the interfering particles (in formula: $\Delta \leq 5d$), most preferably smaller than d ($\Delta \leq d$). In this context, the mean distance between neighboring magnetic particles and/or clusters of magnetic particles in the blocking zone may be defined for example as the smallest distance between neighboring magnetic particles/clusters assuming a homogeneous distribution of all magnetic particles/clusters over the blocking zone in a simple cubic crystal structure. The diameter of a single interfering particle may for example be defined as the diameter of the largest sphere that completely fits into the interfering particle; the "mean diameter" is the average of all these individual particle diameters. When the mean distance $\Delta$ between neighboring magnetic particles/clusters is sufficiently small, the blocking zone will act as a filter for the interfering particles, blocking their transition (almost) completely. For the case of blood as a fluid to be processed and red blood cells as "interfering particles", the mean distance $\Delta$ between magnetic particles in the blocking zone should for example be lower than about 2 µm.

Any kind of processing can be done with the fluid in the processing chamber, including the physical and/or chemical transformation or manipulation of components of the fluid in the bulk. In a preferred embodiment, at least a part of the processing may take place in a region called "processing region" on the surface of the processing chamber, wherein this processing region may extend over the whole surface of the processing chamber or only a limited area which may specifically be prepared.

In the aforementioned embodiment with a processing region, the blocking zone may be located in front of said processing region, thus affecting the migration of interfering particles towards the processing region or away from it (depending on which side of the blocking zone the interfering particles are captured). Hence the concentration of interfering particles at the processing region can be controlled with the help of the blocking zone.

The mentioned processing region is preferably located above the blocking zone with respect to gravity. Sedimentation of interfering particles will then be directed away from the processing region, thus supporting their separation from said region. Gravitational effects on the magnetic particles, which would move the blocking zone away from the processing region, can be compensated for example by magnetic forces.

The processing region may comprise binding sites for target components of the fluid to be processed. Components of interest can then be immobilized in the processing region for further (surface-specific) manipulation and/or detection steps.

Detection or sensing of parameters is one important example for a "processing" of the fluid. In a preferred embodiment of the invention, the processing device may therefore comprise a detection unit for detecting target components of the fluid. In combination with the above embodiments, detection may particularly take place in a processing region at the surface of the processing chamber, and it may particularly relate to target components of the fluid which are bound to the binding sites.

The aforementioned detection unit may optionally comprise an optical, magnetic, mechanical, acoustic, thermal and/or electrical sensor. A magnetic sensor may particularly comprise a coil, Hall sensor, planar Hall sensor, flux gate sensor, SQUID (Superconducting Quantum Interference Device), magnetic resonance sensor, magneto-restrictive sensor, or magneto-resistive sensor of the kind described in the WO 2005/010543 A1 or WO 2005/010542 A2, especially a GMR (Giant Magneto Resistance), a TMR (Tunnel Magneto Resistance), or an AMR (Anisotropic Magneto Resistance). An optical sensor may particularly be adapted to detect variations in an output light beam that arise from a frustrated total internal reflection (FTIR) due to target particles at a sensing surface. This approach is described in more detail in the WO 2008/155716 A1, WO 2009/016533A2, or WO 2008/072156 A2.

The blocking zone may be located in the interior of the processing chamber, thus leaving free passages (for interfering particles) at its periphery. Such a leaky configuration is easy to realize and may be sufficient to achieve a desired inhomogeneous distribution of interfering particles for a limited period of time. The blocking zone may for example constitute a kind of (large) umbrella in front of a (small) detection region such that it effectively keeps the interfering particles away from the processing region while the desired processing steps are taking place.

In a preferred embodiment of the invention, the blocking zone extends between the walls of the processing chamber in such a way that it divides the processing chamber into two disconnected volumes (wherein "disconnected" means that there is no connecting path which runs through the processing chamber without traversing the blocking zone). In this way an inhomogeneous distribution of interfering particles between said two volumes can be maintained for an arbitrarily long duration. If one of the volumes comprises for example the above-mentioned processing region, it is possible to permanently keep the interfering particles away from this.

In one embodiment of the invention, the magnetic particles may be disposed as dry reagents on a surface of the processing chamber before the fluid to be processed is added. This approach is particularly suited when the processing chamber is comprised by some prefabricated element, for example a disposable cartridge used for the investigation of biological samples in some detection device. A user then only has to add a sample fluid at hand to the prefabricated cartridge, and no separate step of addition of magnetic particles is necessary.

If, in the aforementioned embodiment, the processing chamber comprises a processing region at its surface, the magnetic particles may particularly be disposed as dry reagents on said processing region. If a fluid is added to this arrangement, the processing region is shielded from it until the magnetic particles have dissolved. The shielding of the processing region with respect to interfering particles may however be maintained if the dissolving magnetic particles are immediately distributed into a blocking zone in front of the processing region.

In an alternative embodiment, the magnetic particles may be disposed as dry reagents next to a processing region. Fluid added to the processing chamber will then be able to contact the processing region until a blocking zone of magnetic particles may perhaps later affect the distribution of interfering particles within the processing chamber.

The blocking zone may be established at a stationary position within the processing chamber. Alternatively, the blocking zone may be moved within the processing chamber in order to generate some desired distribution of interfering particles. Both a stationary position and a desired movement of the blocking zone may readily be achieved by controlling a magnetic field in the processing chamber accordingly.

The blocking zone may for example be used to collect and/or up-concentrate interfering particles in a certain sub-volume of the processing chamber. When the magnetic particles are initially disposed as dry reagents next to a processing region, the blocking zone (which is created after addition of the fluid and dissolution of the magnetic particles) may be moved in front of the processing region, pushing the interfering particles away from there.

In another embodiment of the invention, the blocking zone of magnetic particles is generated in the processing chamber before the fluid to be processed is introduced. This requires that the magnetic particles are already able to move in some carrier or solvent (e.g. because they were provided as wet reagents and/or because a solvent has been added to a processing chamber comprising magnetic particles as dry reagents). Early generation of a blocking zone of magnetic particles has the advantage that the distribution of interfering particles can be controlled from the beginning, i.e. the moment the fluid is added.

In another embodiment of the invention, magnetic label particles are provided that have binding sites for target components of the fluid to be processed. Accordingly, said target components may specifically bind to the magnetic label particles, allowing to manipulate them by magnetic forces and/or to detect them via properties of the attached magnetic particles. The magnetic label particles may optionally be identical to the magnetic particles that constitute the blocking zone. More generally, there may be magnetic particles that are solely used for establishing the blocking zone and magnetic label particles that are used for binding target components, wherein none, some, or all of the magnetic label particles may in addition be used to create the blocking zone.

The fluid to be processed may particularly comprise a biological fluid, for example saliva, blood, or urine. Such biological fluids typically comprise a huge number of components, wherein some of these components are targets of an assay that is disturbed by other components. With the approach of the present invention, the disturbing components, i.e. the "interfering particles", can be controlled such that their disturbing effects are reduced.

The invention further relates to the use of the processing device described above for molecular diagnostics, biological sample analysis, chemical sample analysis, food analysis, and/or forensic analysis. Molecular diagnostics may for example be accomplished with the help of magnetic beads or fluorescent particles that are directly or indirectly attached to target molecules.

BRIEF DESCRIPTION OF THE DRAWINGS

These and other aspects of the invention will be apparent from and elucidated with reference to the embodiments described hereinafter.

In the drawings:

FIG. 4 schematically illustrates the generation of the blocking zone of magnetic particles that extends between the walls of a processing chamber;

FIG. 5 schematically illustrates a blocking zone of magnetic particles that shields a processing region;

Like reference numbers refer in the Figures to identical or similar components.

DETAILED DESCRIPTION OF EMBODIMENTS

Many biosensors are based on nanoparticle labels, particularly nanoparticles (beads) that can be actuated with electromagnetic fields. Typically, the magnetic beads are functionalized with antibodies that can bind a specific analyte molecule. The beads are attracted to a sensor surface, where the particles can indirectly (by means of a captured analyte) or directly bind to capture probes (e.g. antibodies) printed on the surface. The number of bound beads is directly or inversely related to the amount of analyte molecules present in the sample. The beads can then be detected using any technique that is more sensitive to beads that are close to the surface. For example, the detection technique may be based on evanescent optical fields, e.g. frustrated total internal reflection (FTIR), as in the Magnotech® technology developed by the applicant. Another example is the application of dark field microscopy (DFM).

Figure 1:
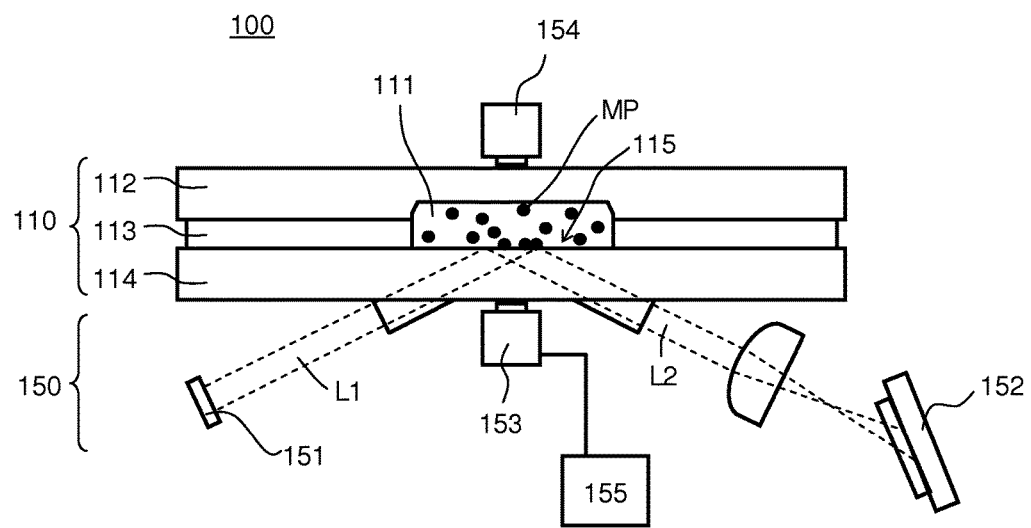
FIG. 1 schematically shows a processing device for the detection of target components in a sample by frustrated total internal reflection.

FIG. 1 shows a schematic side view of an FTIR-based biosensor apparatus 100 that may be used for making examinations on blood. The processing device or sensor apparatus 100 comprises a reader 150 and a disposable cartridge 110. The cartridge 110 may for example be made from glass or transparent plastic like poly-styrene. It comprises a processing chamber 111 in which a sample of blood with target components to be detected (e.g. cardiac troponin, drugs, antibodies, DNA, parathyroid hormone PTH etc.) can be provided. The sample may further comprise magnetic particles MP, for example superparamagnetic beads, wherein these particles are usually bound as labels to the aforementioned target components.

The cartridge 110 comprises a cover 112 and a bottom unit 114 that are separated by a layer 113 of e.g. tape. The cartridge is transparent and has a detection surface 115 that (partially) borders the processing chamber 111. A plurality of processing regions 117 (FIGS. 2-6) are disposed on the detection surface 115. They comprise binding sites 116, e.g. antibodies, which can specifically bind the target components.

The reader 150 comprises a light source 151 for emitting an "input light beam" L1, a light detector 152 for detecting and measuring an "output light beam" L2, and an evaluation unit (not shown) for evaluating the signals of the light detector. The input light beam L1 generated by the light source 151 arrives at the detection surface 115 at an angle larger than the critical angle of total internal reflection (TIR) and is therefore totally internally reflected as the output light beam L2. The output light beam L2 leaves the cartridge 110 and is detected by the light detector, e.g. by the light-sensitive pixels of a camera 152.

The reader 150 further comprises a magnetic field generator, for example electromagnets 153, 154 with a coil and a core disposed at the bottom and/or at the top of the cartridge, for controllably generating a magnetic field at the detection surface 115 and in the adjacent space of the processing chamber 111. The electromagnets 153, 154 are coupled to a controller 155 by which they can be supplied with appropriate currents. With the help of the generated magnetic field, the magnetic particles can be manipulated, i.e. be magnetized and particularly be moved (if magnetic fields with gradients are used). Thus it is for example possible to attract magnetic particles to the detection surface 115 in order to accelerate the binding of the associated target component to said surface.

A typical assay with the apparatus 100 comprises the following steps: (1) Magnetic beads coated with a primary antibody directed against a target component disperse in the sample liquid and bind the target. (2) Top and bottom coils actuate the magnetic particles in a pulsed manner, resulting in binding to the sensor surface where a secondary antibody can bind to the bound target molecule. (3) Non-bound beads are removed from the sensor surface and bound beads are detected using an evanescent field. Further details of this procedure may be found in the WO 2008/115723 A1, which is incorporated into the present text by reference.

When blood samples shall be investigated with a biosensor of the kind described above, a filtering step is usually needed in order to separate blood plasma comprising the target components from blood cells. The disposable cartridge 110 in which the assays are performed may for example contain a filter unit which separates the red blood cells from the plasma, which is transported to the processing chamber with the magnetic particles. Such a filter unit is a relatively expensive part of the cartridge, due to the multiple materials and processes required for its assembly. However, the assays cannot be performed in the presence of red blood cells because i) the magnetic particles can bind non-specifically to the red blood cells and ii) the red blood cells sterically hinder the magnetic particles, inhibiting the movement of the particles and their binding to the sensor surface. Furthermore, the filtering process, followed by capillary filling of the microfluidic channels and processing chambers, is a slow process (it can take up to one minute of the total assay time of five minutes), gives rise to imprecision (through variation in filling times and retention of analyte molecules), and is inefficient (25 μL of blood input only yields 2 μL of plasma output).

In order to address the above problems, it is proposed to use magnetic particles as a filter, thereby avoiding the need for a separate expensive filter unit. By providing a layer with a high density of magnetic particles (multiple particle layers) close to the detection area, the red blood cells or other "interfering particles" are prevented from reaching the detection area and thereby inhibiting the assay.

Figure 2:
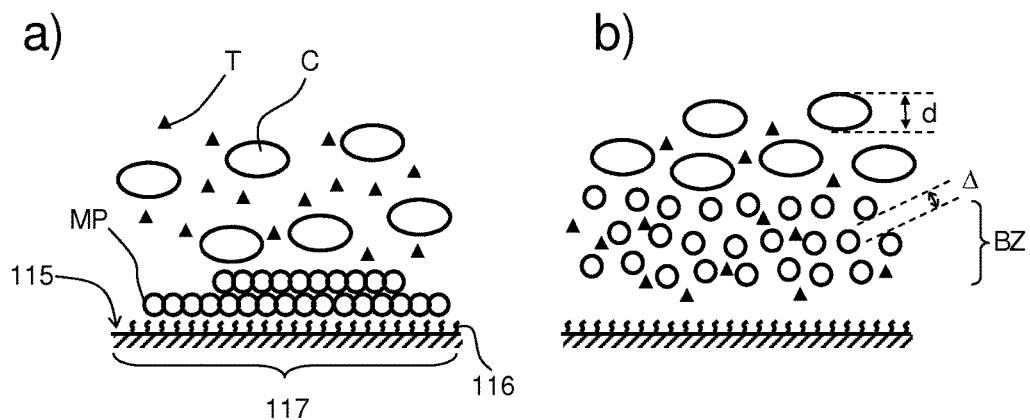
FIG. 2 schematically illustrates the generation of a blocking zone from magnetic particles that are initially deposited on binding sites of a processing region.
Figure 3:
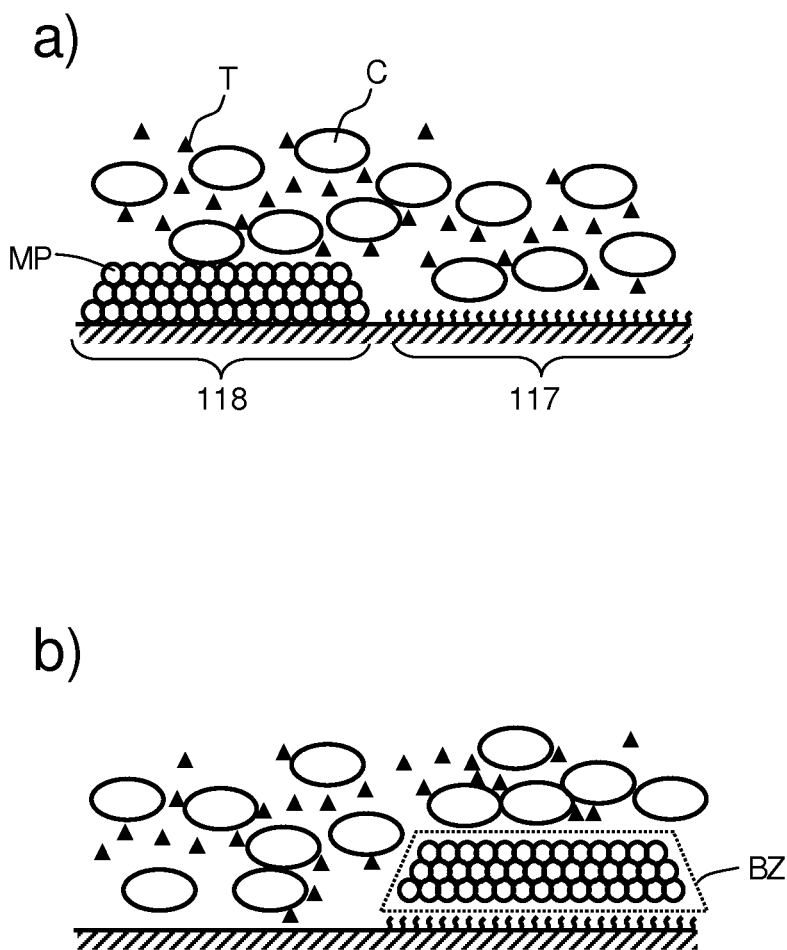
FIG. 3 schematically illustrates the generation of a blocking zone from magnetic particles that are initially deposited next to binding sites of a processing region.

FIG. 2 comprises a schematic drawing of magnetic particles MP functioning as a filter. The magnetic particles MP are supplied in a dry form in a dense layer on top of capture molecules 116 (antibody layer) that are coated in a "processing region" or "binding region" 117 on a sensor surface 115. When the processing chamber is filled with whole blood, the magnetic particles will redisperse.

FIG. 2a) shows the processing chamber immediately after addition of the fluid to be processed, i.e. the sample of blood. The blood sample comprises red blood cells C and target molecules T in the blood plasma.

FIG. 2b) shows the situation upon redispersion of the magnetic particles MP. The magnetic particles distribute into a dense layer of magnetic particles MP, called "blocking zone" BZ in the following. The red blood cells C cannot penetrate this blocking zone, whereas the plasma, containing the target molecule T, can. Thereafter, the magnetic particles can be actuated, during which the topmost particles prevent the red blood cells from interacting with the assay conducted with the bottom particles.

In FIG. 2b), the (mean) diameter d of the interfering particles C as well as the (mean) distance Δ between neighboring magnetic particles MP in the blocking zone BZ are indicated. If Δ≤d, i.e. if the "pores" of the blocking zone are smaller than the interfering particles, it is possible to completely prevent the interfering particles C from passing through the blocking zone.

It should be noted that magnetic beads typically form chains (clusters) in an external magnetic field with a certain gap size between the chains. The "magnetic particles MP" (circles) in the drawings can therefore also be replaced by chains of several individual magnetic particles. The gap size between these chains will then take the role of the aforementioned "distance Δ" (cf. FIG. 7).

While FIG. 2a) shows the application of magnetic particles MP as a dry reagent layer, it is also possible to use wet reagents, in which first a fluid containing the magnetic particles is supplied to a processing chamber. The magnetic particles are then drawn magnetically to a surface, after which the blood is applied to the processing chamber.

The magnetic particles can also be stored at a different location than on top of the capture probes in the binding region. FIG. 3a) shows the case in which they are initially supplied in a location 118 next to the binding region 117 with the capture molecules. When during redispersion the magnetic particles MP remain in a dense layer (e.g. by applying a magnetic field or with short redispersion times), the resulting magnetic particle "plug" or blocking zone BZ can be moved laterally towards the detection area 117 containing the capture probes, thereby pushing red blood cells out of the detection area.

FIGS. 4a)-c) illustrate a way to increase the volume of sample fluid that can be used for an assay. Magnetic particles MP that are (for example) initially stored on the binding sites of the binding region can be pushed (with the help of a magnetic field) as a dense blocking zone BZ against the layer of red blood cells, thereby creating a larger volume from which the red blood cells are excluded (FIG. 4b). Thereafter the assay can be conducted (FIG. 4c). To prevent the red blood cells from moving underneath the magnetic particles, this works best when performed in a constricted area (for example a small chamber), in which there is no room between the magnetic particles and the walls (dashed lines).

Another option is shown in FIG. 5. Here, the dimensions of the blocking zone or layer BZ of magnetic particles MP are much larger than the capture probe layer 117, such that even if some red blood cells C get beneath the magnetic particle layer BZ at its rim, no red blood cells will be present at the center, i.e. at the detection area 117 with capture probes.

Figure 6:
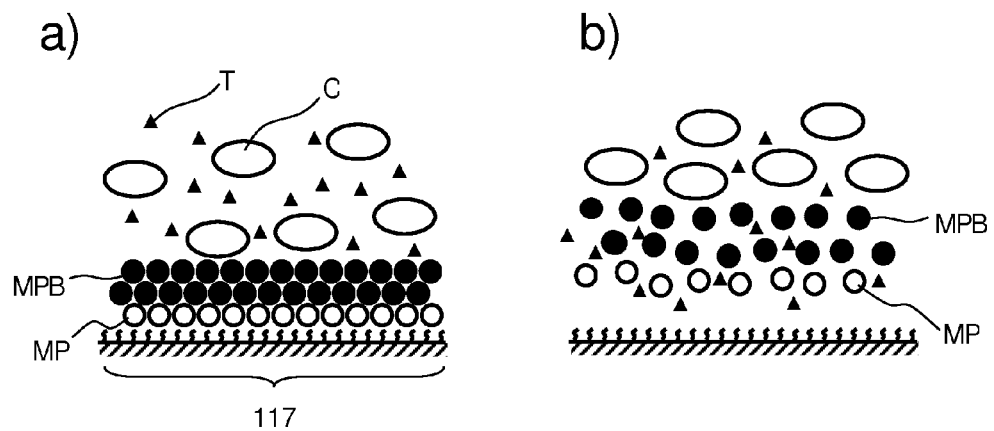
FIG. 6 schematically illustrates the application of magnetic particles for creating a blocking zone and of magnetic label particles.

Instead of using the same magnetic particles as filter and as capture particles that can bind to the sensor surface, two different types of magnetic particles can be used. This is illustrated in FIG. 6, according to which a layer of "magnetic label particles" MP is disposed beneath the layer(s) of (non-functionalized) magnetic particles MPB that constitute the blocking zone BZ. This approach has the advantage that the properties of the upper layers of magnetic particles MP close to the red blood cells C can be chosen independently, e.g. the number of particles, the size of the particles. Furthermore, these magnetic particles do not need to be functionalized with antibodies and will therefore not bind target molecules, resulting in more target molecules available for the detection.

These two layers of magnetic particles MP, MPB can be applied as dry reagents, by first depositing a first layer of first magnetic label particles MP, and then depositing a second layer of second magnetic particles MPB. Alternatively, these can be applied as wet reagents, attracting first the first set of magnetic label particles MP towards the surface and then adding and attracting to the surface a second set of magnetic particles MPB.

Figure 7:
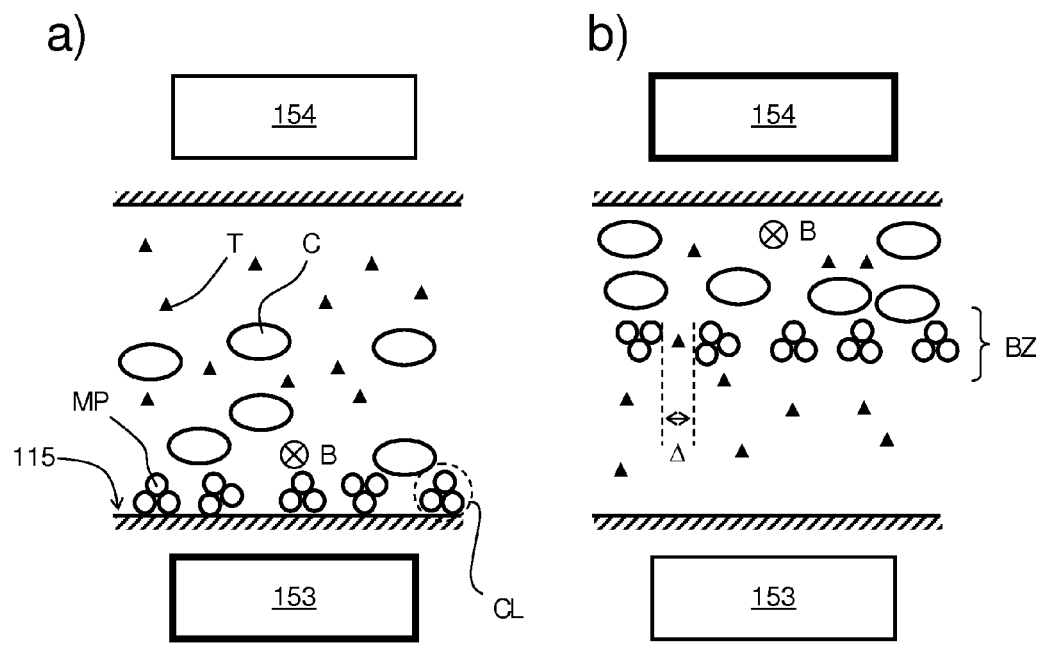
FIG. 7 schematically illustrates the application of magnetic fields parallel to the detection surface and the creation of a blocking zone with clusters of magnetic particles.

FIG. 7 schematically illustrates that the above principles work equally with clusters or chains of magnetic particles instead of single magnetic particles (clusters of magnetic particles will in fact be observed in most cases). Moreover, it is assumed that the applied magnetic fields B are parallel to the detection surface 115.

In FIG. 7a), only the bottom magnet 153 is active. It is assumed that this is a horseshoe magnet 153 (with its poles lying behind each other perpendicular to the drawing plane) that provides a magnetic field B directed parallel to the detection surface 115 (perpendicular to the drawing plane). This implies that the magnetic beads MP will form chains CL parallel to the detection surface 115 when the magnetic field B is switched on. The Figure shows the chains CL in a cross section. Simultaneously a magnetic force is generated which attracts the chains to the surface 115.

Basically the magnetic chains CL will have slight gaps of (mean) width Δ between them. The resulting configuration resembles a one-dimensional grid. As long as the gaps between the chains are smaller than the smallest dimension d of the interfering particles C, no particles C will pass.

In FIG. 7b) the bottom magnet 153 has been switched off and the top magnet 154 has been switched on. If the top magnet would be a cylindrical magnet, a vertical arrangement of the chains of magnetic particles would result, which proves to be less effective in blocking the interfering particles. It is therefore preferred to use a horseshoe magnet also as a top magnet 154. In this case the one-dimensional grid of bead clusters is maintained while they can be moved to the top of the cartridge, 'compressing' the interfering particles C. Thus the blocking zone BZ can effectively be moved.

It should be noted that the described methods can also be used to prevent other large particulates (instead of red blood cells) from interfering with a magnetic particle assay. Moreover, the assays can benefit from a reversed geometry (turning the setups of FIGS. 1-7 upside down with respect to gravity), such that the detection surface is on top and that gravity can move the interfering particles (e.g. red blood cells) substantially away from the detection surface.

The invention can particularly be used in in vitro diagnostic (immuno)assays, e.g. with Philips Magnotech® technology, for the detection of biomarkers in biological samples, such as the detection of cardiac troponin in blood for the diagnosis of acute myocardial infarction.

In the following, an example will be described with respect to FIGS. 8 and 9. Anti cardiac troponin I (cTnI) antibodies were applied to the surface of a plastic cartridge, suitable to be used with the FTIR or DFM detection described above. On top of these antibodies, a large amount of magnetic particles, functionalized with anti-cTnI antibodies, was applied and allowed to dry, thereby forming a dense layer. Blood, spiked with 10 pM cTnI (or without cTnI as a negative control) was applied to the cartridge, while keeping the particles close to the surface using a magnetic field. The magnetic particles were then allowed to capture the cTnI molecules and bind to the surface. A magnetic wash step was used to remove non-bound magnetic particles from the surface, and the amount of magnetic particles bound on the surface were counted using the DFM detection technology (cf. WO 2011/036634A1).

Figure 8:
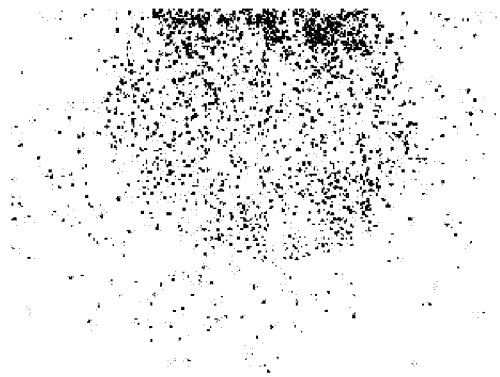
FIG. 8 shows a microscope image of magnetic particles bound to a binding region after an assay in whole blood.

FIG. 8 shows an example of DFM detection particles bound to the surface after an assay with 10 pM cTnI in whole blood. Although also many particles bind outside the area where the anti-cTnI antibodies are printed (circular area on top), the outside signal (normalized to the detection area) can be subtracted from the amount of particles inside the capture spot. Although the assay was unoptimized, 10 pM can clearly be distinguished from the background binding, with an estimated limit of detection of about 1 pM cTnI.

Figure 9:
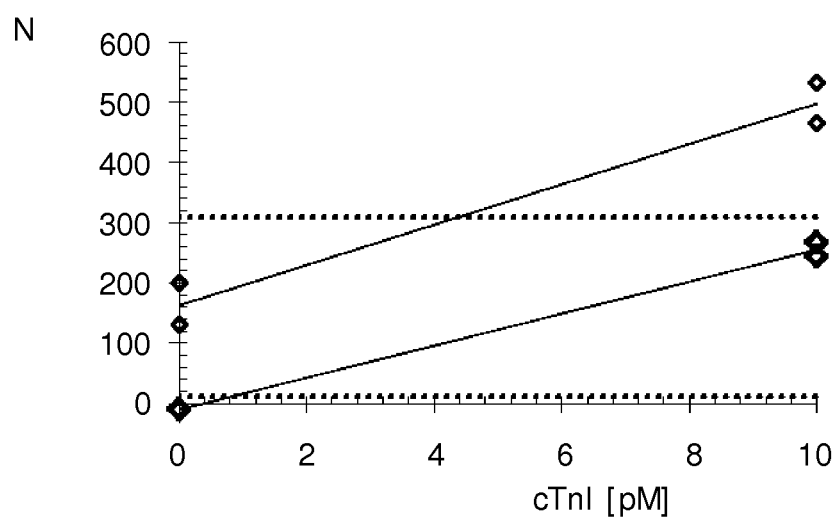
FIG. 9 shows a dose-response-curve obtained in an assay for the detection of target components in a sample.

FIG. 9 shows the resulting dose-response curve showing the detected amount N of particles in samples containing either 0 or 10 pM cTnI. The upper points represent the direct (uncorrected) result, the lower points represent the data, corrected for binding outside the area with anti-cTnI antibodies.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A device for processing a fluid containing interfering particles (C), the device comprising:
   a processing chamber containing the fluid and magnetic particles (MP, MPB), the processing chamber comprising a blocking zone (BZ, BZ') formed by distribution of the magnetic particles for physically imped the interfering particles to filter out and control distribution of the interfering particles within the processing chamber during the processing of the fluid to alter interference caused by the interfering particles; and
   a magnetic field generator for generating a magnetic field that provides, at least in part, the distribution of the magnetic particles (MP, MPB) forming the blocking zone (BZ, BZ') within the processing chamber,
   wherein the mean distance between the magnetic particles (MP, MPB) and/or clusters (CL) of the magnetic particles of the blocking zone (BZ, BZ') is less than or equal to about five times the mean diameter of the interfering particles (C).

2. The device according to claim 1, wherein a surface of the processing chamber comprises a processing region in which the processing of the fluid occurs.

3. The device according to claim 2, wherein the processing region comprises binding sites for target components (T) of the fluid.

4. The device according to claim 1, wherein the blocking zone (BZ, BZ') extends between opposing walls of the processing chamber, dividing the processing chamber into two disconnected volumes.

5. The device according to claim 1, wherein the mean distance between magnetic particles (MP, MPB) and/or clusters (CL) of magnetic particles in the blocking zone (BZ, BZ') is less than or equal to the mean diameter of the interfering particles (C).

6. The device according to claim 1, wherein the blocking zone impedes migration of the interfering particles by maintaining distances between the magnetic particles (MP, MPB) and/or the clusters (CL) of magnetic particles through which interfering particles can not pass.

7. A device comprising:
   a processing chamber that receives a fluid with target components and interfering particles, the processing chamber comprising:
      a detection surface comprising at least one binding site for binding the target components; and
      a blocking zone formed by distributing magnetic particles for physically impeding the interfering particles in the fluid for filtering, thereby controlling distribution of the interfering particles within the processing chamber during processing of the fluid to reduce interference caused by the interfering particles; and
   a magnetic field generator that generates a magnetic field for distributing the magnetic particles to form the blocking zone within the processing chamber.

8. The device of claim 7, wherein the mean distance between the magnetic particles and/or clusters of the magnetic particles of the blocking zone is less than or equal to about five times the mean diameter of the interfering particles.

9. The device of claim 7, wherein the mean distance between the magnetic particles and/or clusters of the magnetic particles of the blocking zone is less than or equal to the mean diameter of the interfering particles.

* * * * *